(12) United States Patent  (10) Patent No.: US 7,824,407 B2
Yamamoto et al.  (45) Date of Patent: Nov. 2, 2010

(54) TREATMENT TOOL FOR ENDOSCOPE

(75) Inventors: Hironori Yamamoto, Simotsuke (JP);
Megumi Kimura, Tokyo (JP); Ichiro Takahashi, Tokyo (JP)

(73) Assignee: Olympus Corporation (JP)

( * ) Notice: Subject to any disclaimer, the term of this patent is extended or adjusted under 35 U.S.C. 154(b) by 861 days.

(21) Appl. No.: 11/553,084

(22) Filed: Oct. 26, 2006

(65) Prior Publication Data

US 2007/0135813 A1    Jun. 14, 2007

(30) Foreign Application Priority Data

Oct. 28, 2005   (JP) .......................... P2005-313659

(51) Int. Cl.
*A61B 18/14* (2006.01)
(52) U.S. Cl. .............. 606/46; 606/49; 606/52
(58) Field of Classification Search ............ 606/41, 606/45, 46, 139–144; 600/49, 104
See application file for complete search history.

(56) References Cited

U.S. PATENT DOCUMENTS

| 2,137,710 | A | * | 11/1938 | Anderson |
| 3,958,576 | A | | 5/1976 | Komiya |
| 4,011,872 | A | | 3/1977 | Komiya |
| 5,527,313 | A | | 6/1996 | Scott et al. |
| 5,647,115 | A | | 7/1997 | Slater et al. |
| 6,123,678 | A | | 9/2000 | Palmer et al. |
| 6,689,122 | B2 | * | 2/2004 | Yamamoto ............... 606/1 |
| 6,767,348 | B2 | * | 7/2004 | Nakada et al. ........... 606/46 |

FOREIGN PATENT DOCUMENTS

| JP | 60-28408 | 8/1985 |
| JP | H05-11913 | 2/1993 |
| JP | H05-42167 | 2/1993 |
| JP | 8-299349 | 11/1996 |
| WO | WO 02/39912 | 5/2002 |
| WO | WO 2004/006789 | 1/2004 |

OTHER PUBLICATIONS

Machine translation of JP05-042167.*
Untranslated Japanese Office Action issued on Feb. 26, 2008 in connection with corresponding Japanese application No. 2005-313659.
English translation of Japanese Office Action issued in connection with 2005-313659 submitted in lieu of statement of relevancy of prior art teachings to the instant application.
European Search Report dated Apr. 27, 2007.
Letter from Associates reporting European Search Report dated May 22, 2007.
European Office Action, Summons to attend oral proceedings issued by the European Patent Office on Mar. 5, 2009 on the corresponding European Patent Application No. 06022407.8.

* cited by examiner

*Primary Examiner*—Lee S Cohen
(74) *Attorney, Agent, or Firm*—Ostrolenk Faber LLP

(57) ABSTRACT

A treatment tool for an endoscope which grasps an object of treatment, includes: a flexible sheath; a forward-and-backward moving section; and elastic grippers, wherein each of the pair of arms includes: a connector; a bent portion; a rectilinear portion; and a distal clasp, wherein in conjunction with the forward and backward movement operation of the forward-and-backward moving section, the distal ends of the pair of arms are deployed when the pair of arms are projected from the distal end of the sheath, the distal ends of the pair of arms are closed by elastic deformation when the pair of arms are moved into the sheath.

15 Claims, 14 Drawing Sheets

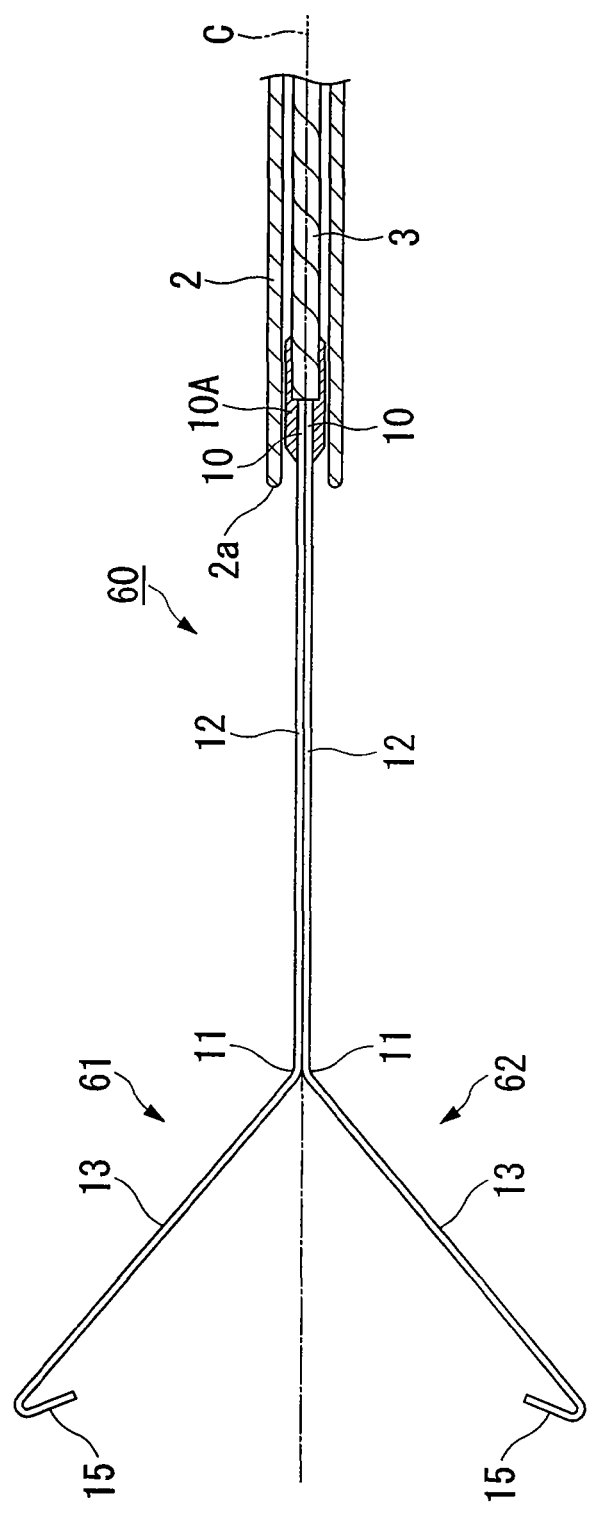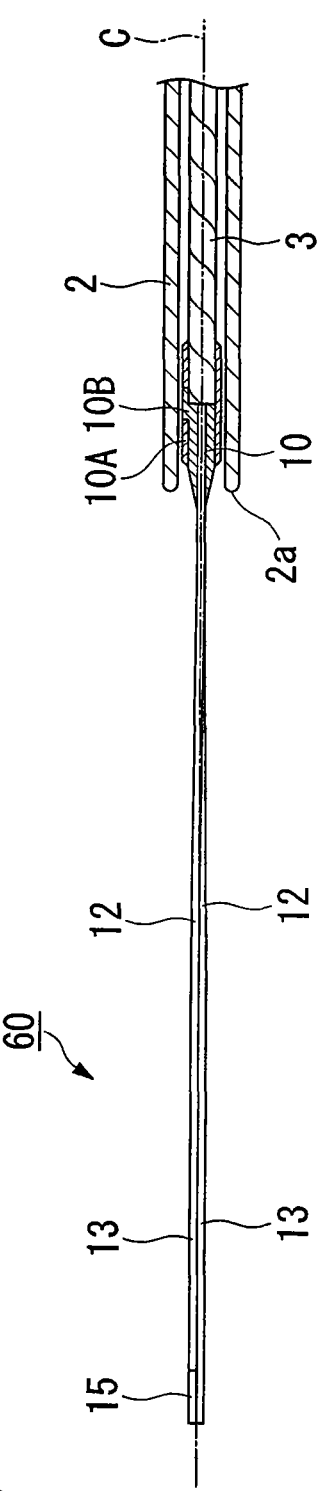
FIG. 15A
FIG. 15B

US 7,824,407 B2

TREATMENT TOOL FOR ENDOSCOPE

BACKGROUND OF THE INVENTION

1. Field of the Invention

The present invention relates to a treatment tool for an endoscope that is inserted into a body cavity through an endoscope, and that conducts a prescribed treatment.

Priority is claimed on Japanese Patent Application No. 2005-313659, filed Oct. 28, 2005, the content of which is incorporated herein by reference.

2. Description of Related Art

There is known to be a treatment tool for an endoscope that is inserted into a body cavity via the channel of an endoscope, and that grasps a diseased portion of biopsy tissue which is the object of treatment.

As this type of treatment tool, a high-frequency treatment tool has been proposed that performs removal or coagulation of diseased portions by conduction of high-frequency current to the grasped diseased portion.

For example, the high-frequency treatment tools disclosed in Japanese Unexamined Utility Model Application, First Publication No. H05-11913 and Japanese Unexamined Patent Application, First Publication No. H05-42167 includes a flexible sheath, a forward-and-backward moving section capable of freely moving forward and backward relative to the sheath, and a pair of arms that is connected to the forward-and-backward moving section and that opens/closes and grasps a diseased portion by having the forward-and-backward moving section move along the sheath. A distal clasp is disposed at the distal end of each of the pair of arms. The distal clasp firstly engages with the diseased portion when the diseased portion is grasped.

According to the distal clasps with which this high-frequency surgical tool is provided, even if a diseased portion has a size such that snares or the like cannot grasp, it is possible to cauterize the diseased portion by conduction of high-frequency current after grasping the diseased portion with the pair of arms.

SUMMARY OF THE INVENTION

The treatment tool for an endoscope according to this invention includes: a flexible sheath; a forward-and-backward moving section disposed inside the sheath so as to be capable of freely moving forward and backward, and having a distal end; and elastic grippers having a pair of arms whose proximal ends are connected to the distal end of the forward-and-backward moving section, wherein each of the pair of arms includes: a connector connecting with the forward-and-backward moving section; a bent portion disposed closer to the distal end than the connector, and bent at a fixed angle relative to the forward and backward directions of the forward-and-backward moving section; a rectilinear portion maintaining the angle from the bent portion and extending linearly toward the distal end; and a distal clasp disposed at the distal end of the rectilinear portion, engaging with the object of treatment, wherein in conjunction with the forward and backward movement operation of the forward-and-backward moving section, the distal ends of the pair of arms are deployed when the pair of arms are projected from the distal end of the sheath, the distal ends of the pair of arms are closed by elastic deformation when the pair of arms are moved into the sheath.

It is preferable that, in the treatment tool for an endoscope of the aspect of this invention, the pair of arms include parallel portions arranged between the connectors and the bent portions.

It is preferable that, in the treatment tool for an endoscope of the aspect of this invention, an angle of the bent portion be an angle which enables the rectilinear portions to rotate toward a direction parallel to the direction of forward or backward movement of the forward-and-backward moving section when the rectilinear portions contact the distal end of the sheath while the forward-and-backward moving section is moved backward along the sheath.

It is preferable that, in the treatment tool for an endoscope of the aspect of this invention, the rectilinear portion of one arm of the arms rotate within a first plane including the rectilinear portion, and the rectilinear portion of the another arm of the arms rotates within a second plane which is parallel to the first plane.

It is preferable that, in the treatment tool for an endoscope of the aspect of this invention, the parallel portions of the pair of arms be respectively arranged to be mutually parallel in a plane which is orthogonal to a plane in which at least one of the arms rotates.

It is preferable that, in the treatment tool for an endoscope of the aspect of this invention, each of the connectors of the pair of arms be arranged to be mutually parallel in a plane which is parallel to a plane in which at least one of the arms rotates.

It is preferable that, in the treatment tool for an endoscope of the aspect of this invention, the inner diameter of the distal end of the sheath be greater than that of the proximal end of the sheath.

It is preferable that, in the treatment tool for an endoscope of the aspect of this invention, the distal clasps be formed by bending at a sharp angle relative to the rectilinear portions in the direction of the inner diameter of the sheath so as to be disposed closer to the connectors than the distal ends of the rectilinear portions.

It is preferable that, in the treatment tool for an endoscope of the aspect of this invention, the forward-and-backward moving section be connected to a treatment energy generator which supplies treatment energy to the pair of arms.

It is preferable that, in the treatment tool for an endoscope of the aspect of this invention, the outer circumferential length of the respective distal ends of the pair of arms including at least the distal clasps be equal to or less than 1.1 mm.

BRIEF DESCRIPTION OF THE DRAWINGS

FIG. 15A is a plan view including a partial cross-sectional view showing a state in which the elastic grippers of the high-frequency surgical tool pertaining to a sixth embodiment of this invention are deployed, and FIG. 15B is a side view including a partial cross-sectional view showing a state in which the elastic grippers of the high-frequency surgical tool pertaining to a sixth embodiment of this invention are deployed.

DESCRIPTION OF THE PREFERRED EMBODIMENT

A first embodiment of this invention is described with reference to FIGS. 1 to 5.

The treatment tool for an endoscope of this embodiment is a high-frequency surgical tool for grasping and cauterizing a diseased portion (object of treatment) such as a polyp that, for example, projects from the surface of biopsy tissue inside a body cavity.

Figure 1:
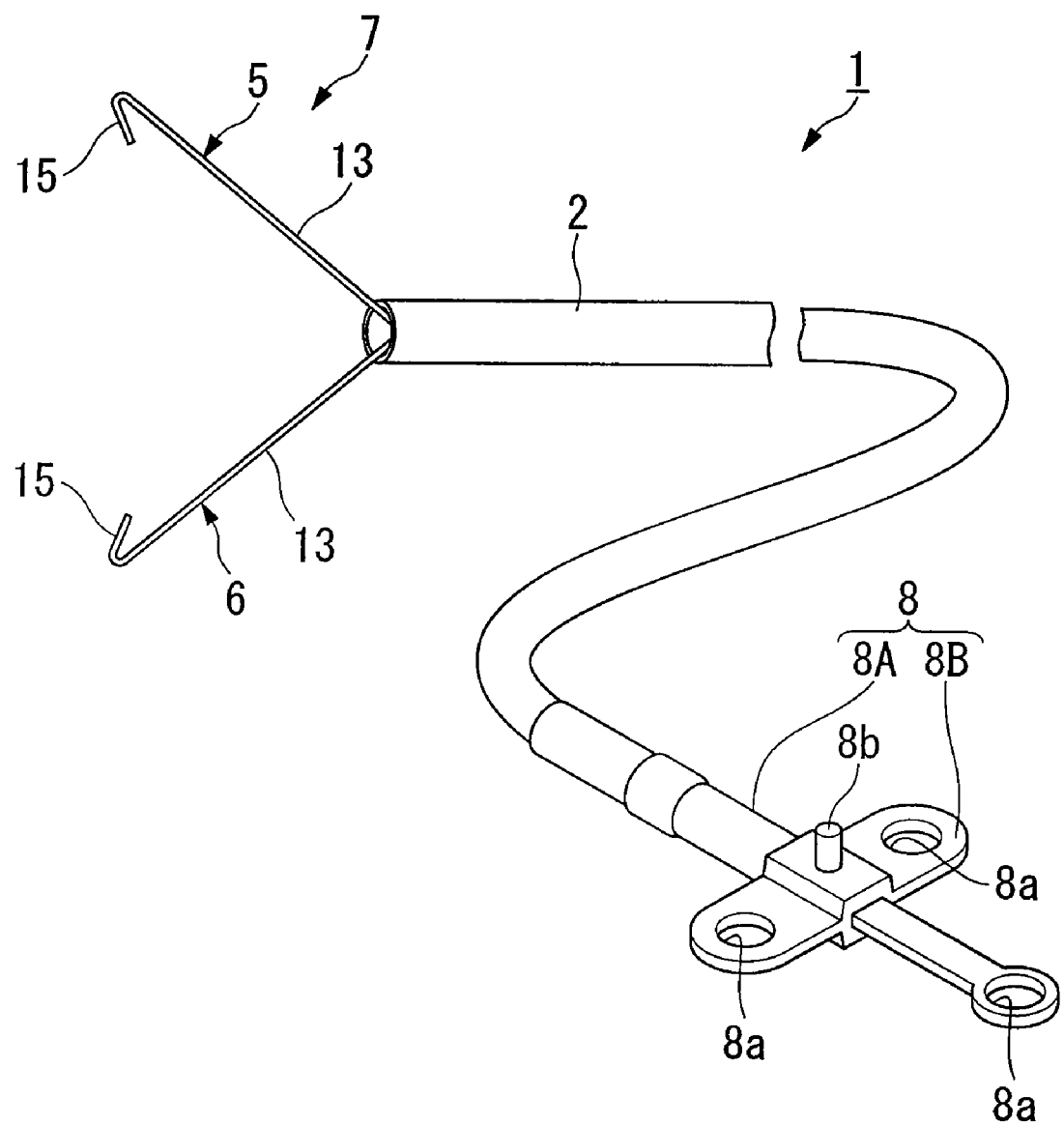
FIG. 1 is a schematic view showing the entirety of the high-frequency surgical tool pertaining to a first embodiment of this invention.
Figure 2:
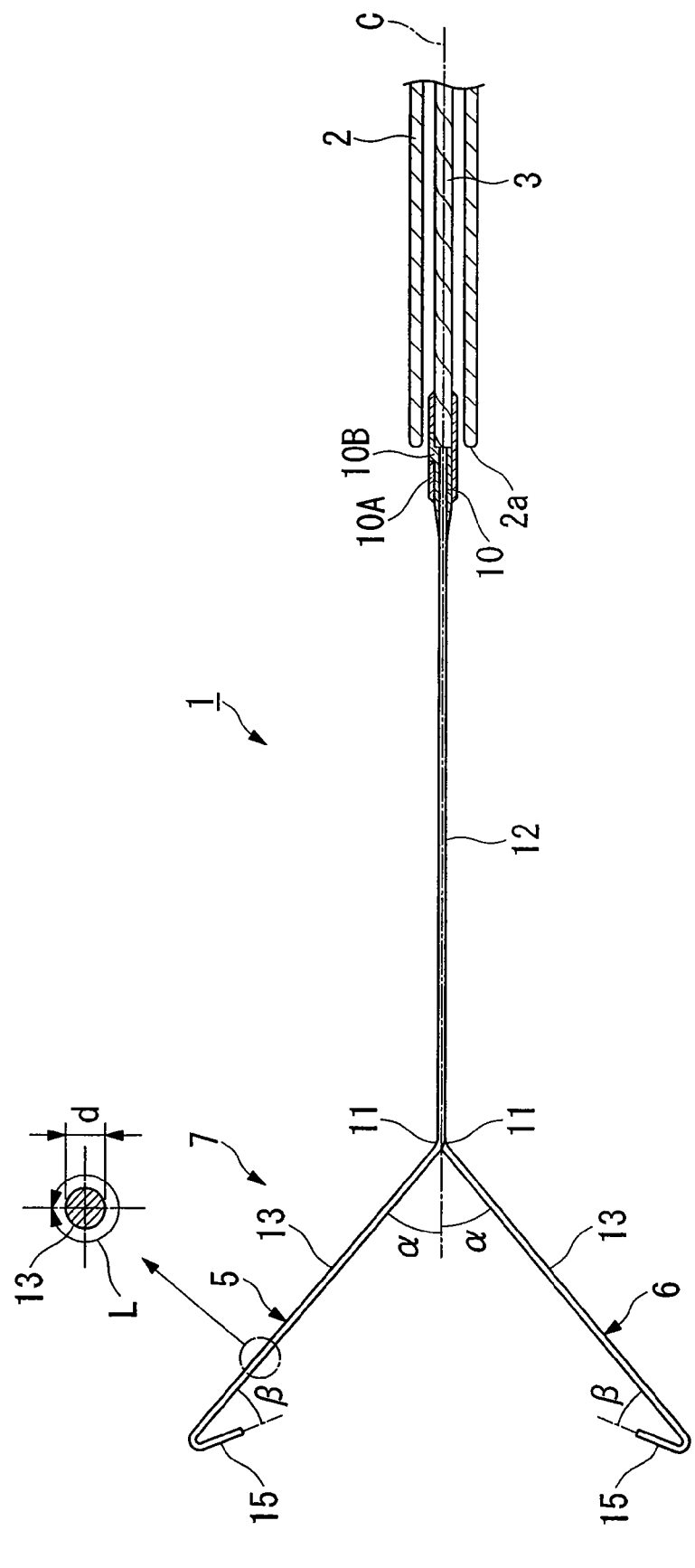
FIG. 2 is a plan view including a partial cross-sectional view showing a state in which the elastic grippers of the high-frequency surgical tool pertaining to the first embodiment of this invention are deployed.
Figure 3A:
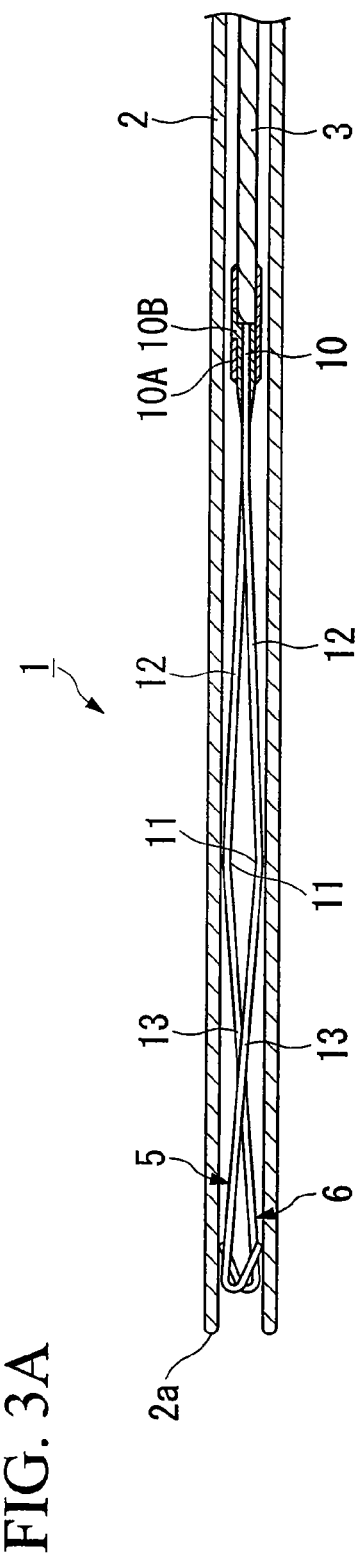
FIGS. 3A to 3C are a cross-sectional views showing a state in which the elastic grippers of the high-frequency surgical tool pertaining to the first embodiment of this invention are stored inside the sheath.
Figure 3B:
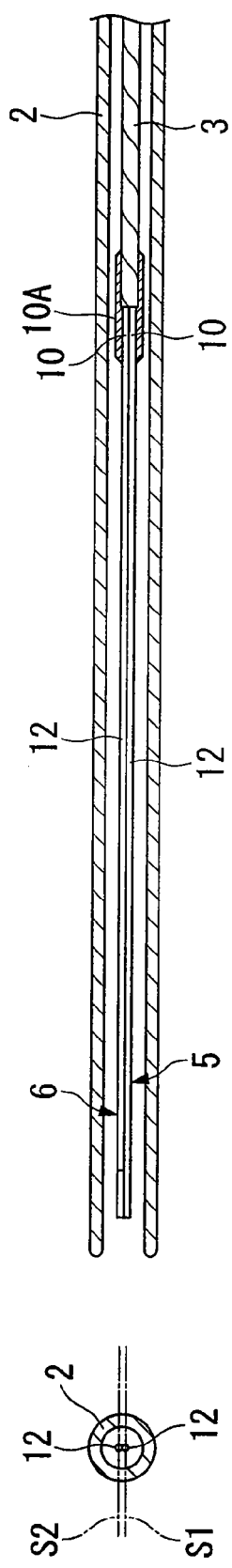
Figure 3C:
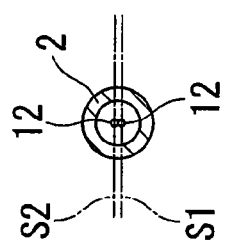

As shown in FIGS. 1 to 3, a high-frequency surgical tool 1 of this embodiment includes: a flexible sheath 2; a control wire 3 (forward-and-backward moving section) disposed so as to freely move forward and backward inside the sheath 2; elastic grippers 7; and a controller 8.

The sheath 2 is formed from a tube, and is capable of being inserted into the channel of an endoscope (not shown).

The control wire 3 possesses electrical conductivity, and is a single-line wire formed so as to have the prescribed low torsional rigidity. Even twisted wire with twisted filaments is acceptable if it has the low torsional rigidity.

The controller 8 is connected to the proximal end of the sheath 2, and controls the forward and backward movement of the control wire 3 relative to the sheath 2.

The elastic grippers 7 have a pair of arms 5 and 6. Proximal ends of the pair of arms 5 and 6 are connected to the tip of the control wire 3 in a state in which their distal ends are deployed when they emerge from the tip of the sheath 2 in conjunction with the forward and backward movement of the control wire 3. The pair of arms 5 and 6 is closed by elastic deformation when they are moved into the sheath 2.

Each of the pair of arms 5 and 6 pertaining to the elastic grippers 7 includes: a connector 10 connecting with the control wire 3; a bent portion 11; a parallel portion 12; a rectilinear portion 13; and a distal clasp 15.

The bent portion 11 is disposed closer to the distal end than is the connector 10, and is bent at a fixed angle a in the direction of movement of the control wire 3, that is, in the direction of axis C of the sheath 2.

The parallel portion 12 is disposed between the connector 10 and bent portion 11, and fixes the interval between the pair of arms.

The rectilinear portion 13 maintains angle a from the bent portion 11, and linearly extends toward the distal end.

The distal clasp 15 is disposed at the tip of the rectilinear portion 13, and strikes the diseased portion.

In other words, the bent portion 11 and parallel portion 12 of each of the pair of arms 5 and 6 are provided so as to be mutually independent, and are mutually connected to the connector 10.

The pair of arms 5 and 6 is configured with elastic linear members that possess conductivity, and is composed from the connectors 10, parallel portions 12, rectilinear portions 13 and distal clasps 15. The wire diameter of the arms 5 and 6 is from 0.26 mm to 0.35 mm (shown by d in FIG. 2).

The cross-sectional shape of the arms 5 and 6 is not limited to a circular shape, and the cross-sectional shape may be elliptical, rectangular or otherwise polygonal, so long as the circumferential length at the distal ends of the pair of arms 5 and 6 including at least the distal clasps 15 is less than or equal to 1.1 mm (shown by L in FIG. 2).

The tips of the connectors 10 and control wire 3 are respectively inserted into a short tube 10A from both ends thereof and joined, and the periphery is covered with an adhesive 10B, whereby they are mutually fastened and connected. Instead of the adhesive 10B, soldering or brazing material is also acceptable, and fastening by simple caulking is also acceptable. The length of the parallel portion 12 is 30 mm from the connector 10. This length may be in a range from 25 mm to 40 mm.

When the planes formed by the respective rectilinear portions 13 and the respective bent portions 11 of the pair of arms 5 and 6 respectively constitute a first deployment plane S1

(first plane) and a second deployment plane S2 (second plane), the first deployment plane S1 and second deployment plane S2 are parallel.

At this time, the rectilinear portion 13 of the arm 5 rotates in the first deployment plane S1, and the rectilinear portion 13 of the arm 6 rotates in the second deployment plane S2.

The respective parallel portions 12 of the pair of arms 5 and 6 are arranged so as to be mutually parallel to a plane that is orthogonal to the first deployment plane S1 and second deployment plane S2.

The bent portions 11 are formed at an angle that enables rotation in a direction parallel to the direction of forward or backward movement of the control wire 3 by contact of the rectilinear portion 13 with the distal face 2a of the sheath 2 when the control wire 3 moves backward relative to the sheath 2.

In other words, the rectilinear portions 13 of the pair of arms 5 and 6 are formed so as to bend in a direction in which they are respectively separated at angle α relative to the axis C. The angle α at this time is 40 degrees. This angle may be in a range from 35 degrees to 45 degrees. The rectilinear portions 13 are formed so as to extend for a length of 20 mm from the bent portions 11. The length may be in a range from 15 mm to 25 mm.

The distal clasps 15 disposed at the tips of the rectilinear portions 13 have a length of 2.0 mm from the tip of the rectilinear portions 13, and are formed such that they are bent at an angle β of 25 degrees relative to the rectilinear portions 13 toward the inner diameter direction of the sheath 2 so as to be disposed closer to the connectors 10 than are the tips of the rectilinear portions 13.

The length of the distal clasps 15 may be in a range from 1.5 mm to 2.5 mm, and the angle β relative to the rectilinear portions 13 may be in a range from 20 degrees to 40 degrees.

The controller 8 includes a controller body 8A extending in the direction of the axis C of the control wire 3, and a sliding portion 8B connected to the proximal end of the control wire 3 and freely moving forward and backward relative to the controller body 8A.

Both the controller body 8A and sliding portion 8B include finger catches 8a enabling finger application.

The sliding portion 8B includes a connection terminal 8b for connection of the below-mentioned high-frequency power source 19 and conducting cable.

Figure 4:
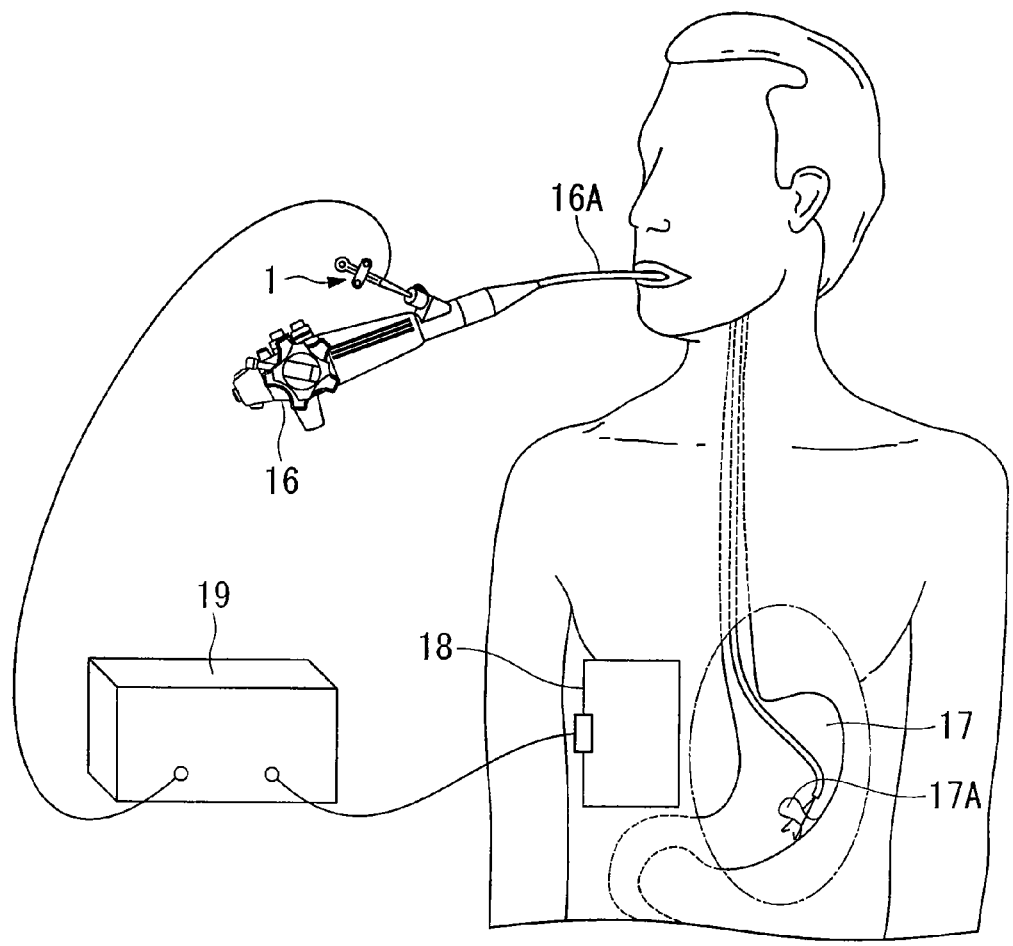
FIG. 4 is an explanatory view showing an outline of the entire system when the high-frequency surgical tool pertaining to the first embodiment of this invention is used.

As shown in FIG. 4, when the high-frequency surgical tool 1 is inserted into an insertion portion 16A of an endoscope 16 that has been inserted into a body cavity, and when the high-frequency surgical tool 1 contacts a diseased portion 17A of biopsy tissue 17, a counter-electrode plate 18 is set up on the body surface so as to face opposite the high-frequency surgical tool 1. Furthermore, a high-frequency power source 19 (treatment energy generator) for supplying treatment energy to the pair of arms 5 and 6, the diseased portion 17A, and the counter-electrode plate 18 are respectively set up so as to form a closed loop with respect to the path of high-frequency current.

Next, the method of use and the operation/results of the high-frequency surgical tool 1 of this embodiment are described.

The method of use of the high-frequency surgical tool 1 includes: a process in which the endoscope 16 is inserted into the body cavity, and the high-frequency surgical tool 1 is inserted into the channel (not shown) of the endoscope 16; a process in which the elastic grippers 7 are made to project from the distal end of the sheath 2 until the pair of arms 5 and 6 is completely deployed; a process in which the tips of the rectilinear portions 13 are pressed against the surface of the biopsy tissue 17 in the vicinity of the diseased portion 17A, and the rotational angle of each deployment plane S1 and S2 is adjusted relative to the sheath 2; a process in which the pair of arms 5,6 is closed, and the diseased portion 17A is grasped; and a process in which high-frequency current is conducted to the pair of arms 5 and 6.

Each process is described below.

First, in the insertion process, the distal end of the sheath 2 is made to project to the vicinity of the diseased portion 17A from the distal end of the insertion portion 16A of the endoscope 16.

During this process, the sliding portion 8B of the controller 8 is withdrawn to the hand grip side which is the proximal end relative to the controller body 8A, and the elastic grippers 7 are completely stored inside the sheath 2.

After the distal end of the endoscope 16 reaches the vicinity of the diseased portion 17A, a cable (not shown) is connected to the connection terminal 8b, the entirety of the sheath 2 is moved along the channel, and the distal end of the sheath 2 is made to protrude to the vicinity of the diseased portion 17A.

Next, the process in which the elastic grippers 7 are projected is performed.

First, the sliding portion 8B is pushed out toward the distal end relative to the controller body 8A until the pair of arms 5 and 6 is completely deployed, and a portion of the parallel portions 12 project from the distal end of the sheath 2.

Figure 5:
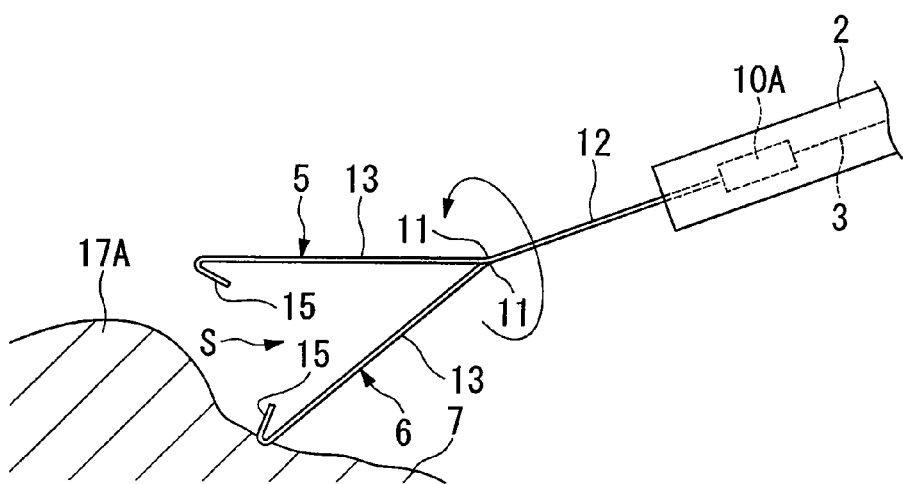
FIG. 5 is an explanatory view showing the method of use of the high-frequency surgical tool pertaining to the first embodiment of this invention.

At this time, depending on the approach of the insertion portion 16A of the endoscope 16 as shown in FIG. 5, there is a case in which the respective deployment planes S1 and S2 of the pair of arms 5 and 6 are inclined relative to the direction of projection of the biopsy tissue 17 of the diseased portion 17A.

In this state, it is impossible to insert the diseased portion 17A between each deployment plane S1 and S2 and grasp it.

In this case, the process in which the angle of rotation of each deployment plane S1 and S2 is adjusted is performed.

First, the tip of the rectilinear portion 13 of either arm of the pair of arms 5 and 6 (in the drawing, it is the arm 6) is pressed against the biopsy tissue 17, and, using it as a fulcrum, manipulation of the torsion and curvature of the insertion portion 16A of the endoscope 16 is conducted.

At this time, as the torsional rigidity of the control wire 3 is low, it is not only the parallel portion 12 that twists, but also the control wire 3.

In this manner, the elastic grippers 7 are made to rotate to the prescribed orientation, and the diseased portion 17A is inserted between the respective deployment planes S1 and S2.

Figure 6A:
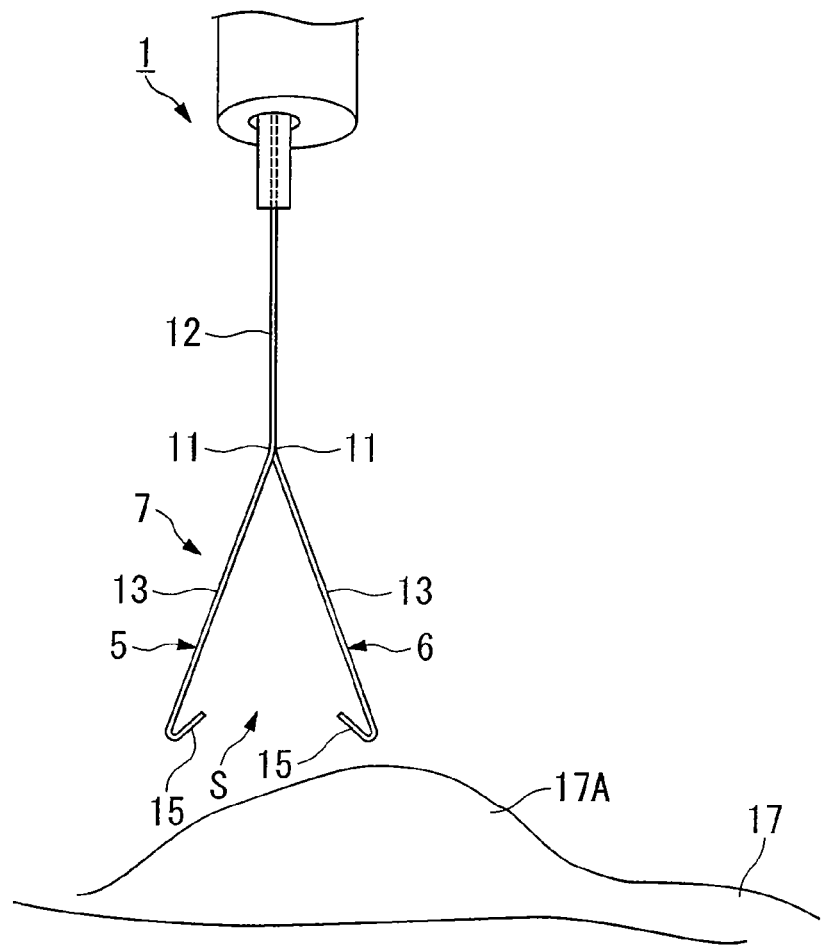
FIGS. 6A and 6B are explanatory views showing the method of use of the high-frequency surgical tool pertaining to the first embodiment of this invention.
Figure 6B:
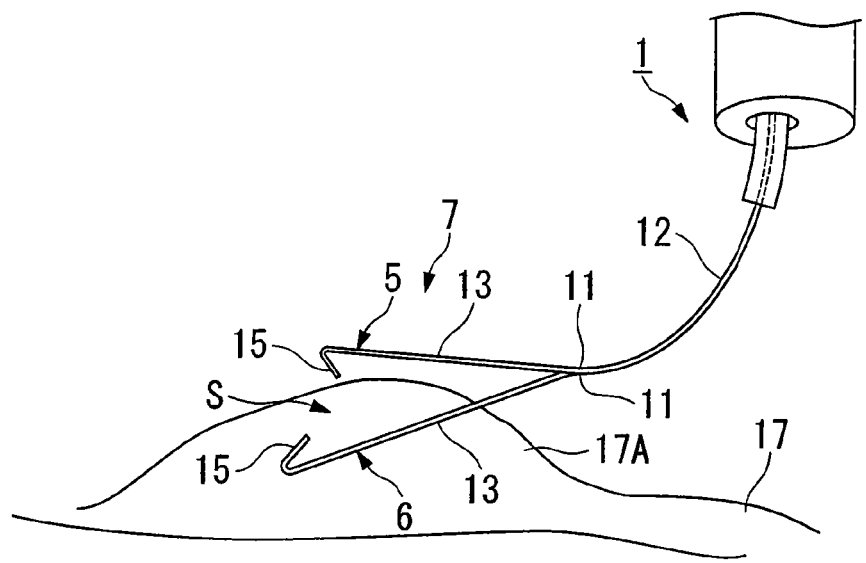

For example, as shown in FIG. 6A, if the insertion portion 16A is inserted at a large angle relative to the biopsy tissue 17 (e.g., from an approximately vertical direction), as shown in FIG. 6B, the insertion portion 16A is manipulated to a state in which the distal ends of both rectilinear portions 13 of the pair of arms 5 and 6 are pressed against the biopsy tissue 17, and the parallel portions 12 are made to bend.

Specifically, by turning and bending the rectilinear portions 13 around an axis that is parallel to the deployment planes S1 and S2 and that is orthogonal to the direction of forward or backward movement of the pair of arms 5 and 6, the diseased portion 17A may be inserted between the respective deployment planes S1 and S2.

The process in which the diseased portion 17A is sandwiched is performed.

Figure 7A:
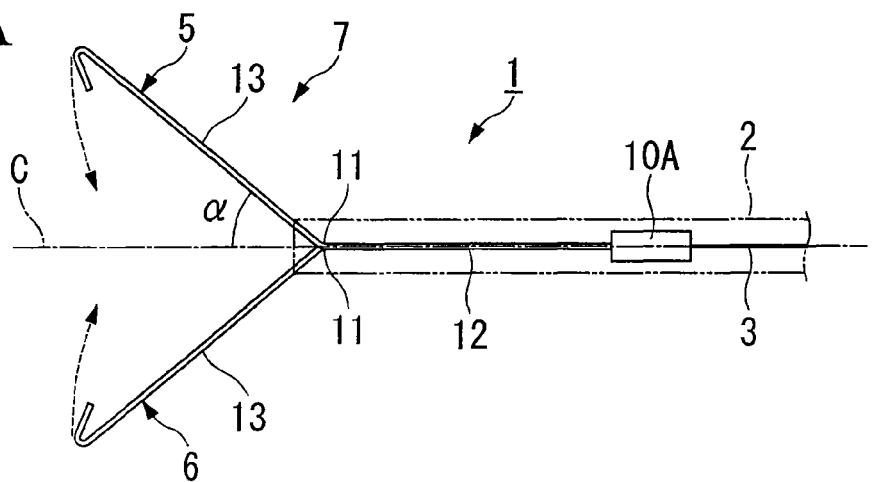
FIG. 7A is a plan view showing a state in which the high-frequency surgical tool pertaining to the first embodiment of this invention is deployed.

First, the sliding portion 8B is withdrawn to the handgrip side relative to the controller body 8A. The parallel portions 12 are moved into the sheath interior. After this movement, there is further backward movement, the rectilinear portions 13 of the pair of arms 5 and 6 contact the distal face 2a of the sheath 2 in a state in which they maintain the angle α, as shown in FIG. 7A.

Figure 7B:
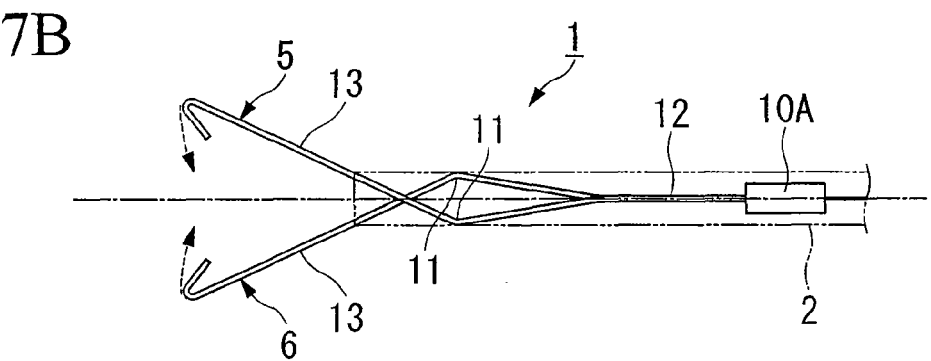
FIG. 7B is a plan view showing a state in which the high-frequency surgical tool pertaining to the first embodiment of this invention is withdrawn.
Figure 7C:
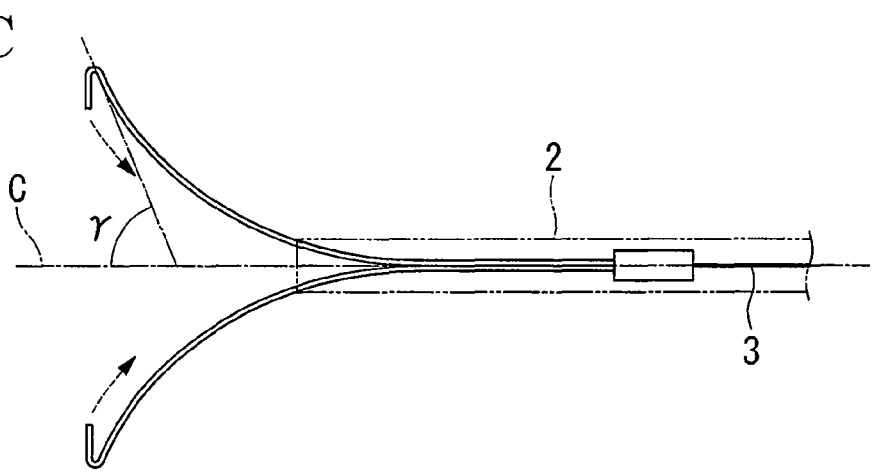
FIG. 7C is a plan view showing a state in which a conventional high-frequency surgical tool is deployed.

Here, in the case of the conventional high-frequency surgical tools disclosed in Japanese Unexamined Utility Model Application, First Publication No. H05-11913 and Japanese Unexamined Patent Application, First Publication No. H05-42167, the arms smoothly curve as shown in FIG. 7C.

That is, the angle constituted by the tangent and axis at a desired position of the arms is continuously changed so as to gradually enlarge from the proximal end of the arms to the distal end, and is greatest at the distal end.

Consequently, when the control wire 3 is withdrawn into the sheath 2 and the arms are closed, the angle γ constituted by the tangent and the axis C of the arms in the vicinity of the distal clasps gradually only decreases with the withdrawal of the control wire 3 into the sheath 2.

That is, although the distal clasps draw closer to the sheath 2 when the control wire 3 is first moved backward toward the handgrip side, the amount of movement toward the axis C of the distal clasps is small.

Figure 7D:
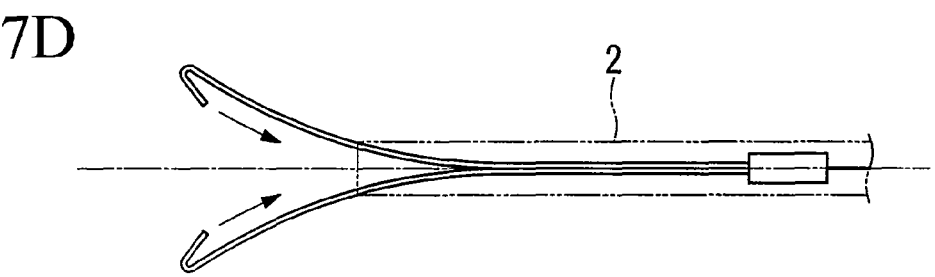
FIG. 7D is a plan view showing a state in which the conventional high-frequency surgical tool is withdrawn.

Accordingly, as shown in FIG. 7D, as the distal clasp approach the sheath 2, the axis C is first approached, the pair of arms is closed, and the recessed amount of control wire becomes large.

However, in the case of the high-frequency surgical tool 1, as shown in FIG. 7B, as a result of the withdrawal of the control wire 3, the rectilinear portions 13 press against the distal sheath face 2a, and the relative position of the bent portions 11 vis-à-vis the sheath 2 moves from on the axis C of the sheath 2 to the inner circumferential face.

During this time, the distal clasps 15 approach the direction of the axis C due to the abrupt contraction of the angle α to the prescribed angle and due to the rotation of the rectilinear portions 13.

When the control wire 3 is further withdrawn, the rectilinear portions 13 further rotate in a direction parallel with the axis C with the bent portions 11 as the center of rotation, and the angle α contracts.

In this manner, the pair of arms 5 and 6 is closed even though the amount of withdrawal of the control wire 3 is smaller than in the conventional cases.

The control wire 3 is then further withdrawn toward the handgrip side, and the diseased portion 17A is sandwiched between the distal clasps 15 and the distal end of the rectilinear portions 13 and the distal face 2a of the sheath 2.

In this state, the process in which high-frequency current is conducted to the pair of arms 5 and 6 is performed, the prescribed high-frequency current is conducted from the high-frequency current generator 19, and the diseased portion 17A is cauterized.

In this manner, the diseased portion 17A can be removed or coagulated.

Moreover, the member that has been removed by cauterization is grasped and recovered by the distal clasps 15, and evacuated outside the body.

In this instance, the high-frequency surgical tool 1 functions as a grasping forceps.

According to this high-frequency surgical tool 1, it is possible to close the pair of arms 5 and 6 even if the amount of withdrawal of the control wire 3 is small.

Accordingly, in the period until closure of the pair of arms 5 and 6, it is possible to reduce the movement amount of the distal clasps 15 in the withdrawal direction, that is, the movement amount in the direction going away from the diseased portion 17A.

By this means, the diseased portion 17A can be reliably grasped by the pair of arms 5 and 6 at the desired position without slippage of the diseased portion 17A in the distal clasps 15.

Moreover, as at least the outer circumferential length L of the distal clasps 15 is equal to or less than 1.1 mm, it is possible to raise the current density of the high-frequency current at the distal ends of the pair of arms 5 and 6, and to perform highly efficient cauterization by generating greater joule heat.

Furthermore, as the parallel portions 12 are arranged in the high-frequency surgical tool 1, the elastic deformation of the pair of arms 5 and 6 closed (folded) inside the sheath 2 can be generally dispersed from the bent portions 11 to the parallel portions 12 and connectors 10.

Accordingly, there is no instantaneous release of elastic force even when the arms 5 and 6 are made to project from the sheath 2.

As a result, the deployment width of the arms can be easily adjusted, and it is possible to greatly reduce any surprise of the observer at abrupt operation.

Moreover, when the elastic grippers 7 are moved into the sheath 2, the distal clasps 15 bend in the aforementioned manner relative to the rectilinear portions 13, with the result that the pair of arms 5 and 6 can be stored inside the sheath 2 without the distal clasps 15 catching on the distal face 2a of the sheath 2 even if they are long.

Accordingly, it is possible to obtain adequate length to the distal clasps 15.

Figure 8:
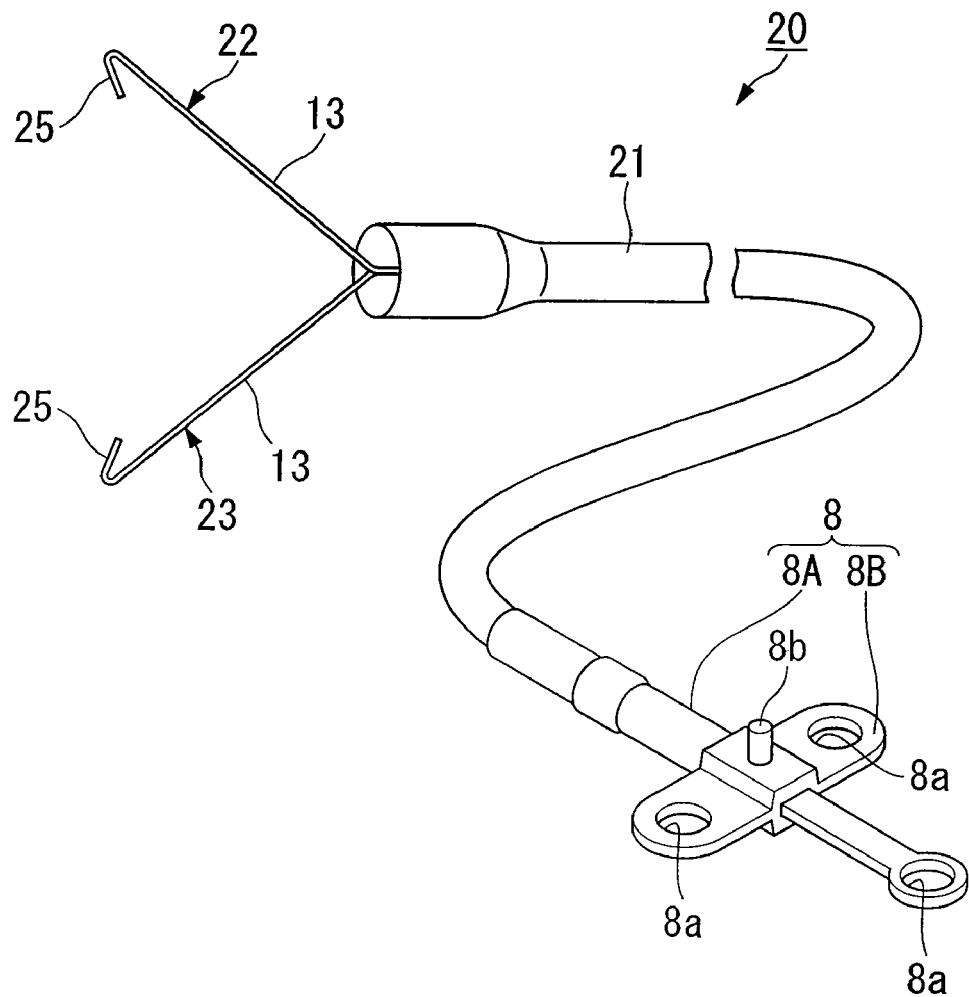
FIG. 8 is a schematic view showing the entirety of the high-frequency surgical tool pertaining to a second embodiment of this invention.
Figure 9:
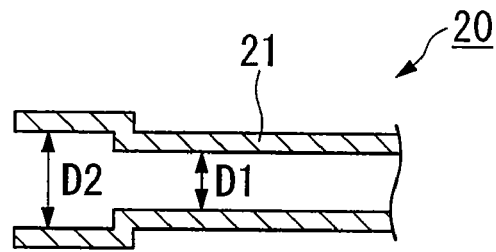
FIG. 9 is a cross-sectional view showing the distal end of the sheath of the high-frequency surgical tool pertaining to the second embodiment of this invention.

Next, a second embodiment is described with reference to FIGS. 8 and 9.

Components identical to those of the above-described first embodiment are given the same reference numerals, and description thereof is omitted.

The point of difference between the first embodiment and the second embodiment is that the inner diameter in the vicinity of the distal end of the sheath 21 of the high-frequency surgical tool 20 of this embodiment is greater than the inner diameter at its proximal end.

With the high-frequency surgical tool 20 of this embodiment, for example, while the inner diameter D1 of the proximal end of the sheath 21 is 1.3 mm to 1.7 mm, the inner diameter D2 at its distal end is 2.0 mm to 2.6 mm.

Here, it is acceptable for the inner diameter D2 to be approximately 1.6 times the inner diameter D1.

The length of the distal clasps 25 from the rectilinear portions 13 on the pair of arms 22 and 23 is extended to 2.5 mm from the 2.0 mm of the first embodiment.

Furthermore, the angle of bending relative to the rectilinear portions 13 is expanded from 25 degrees to 35 degrees.

It is acceptable for the length of the distal clasps 25 to be 2.0 mm to 3.0 mm, and for the angle β relative to the rectilinear portions 13 to be in the range of 30 degrees to 50 degrees.

According to this high-frequency surgical tool 20, when the pair of arms 22 and 23 are closed in order to be stored inside the sheath 21, the distal clasps 25 can be stored inside the sheath 21 even if the length of the distal clasps 25 are longer than in the case of the first embodiment as mentioned above.

Accordingly, it is possible to ensure adequate length for purposes of grasping even when the diseased portion 17A is large.

In this instance, as the only the distal end of the sheath 21 is given a large diameter, it is possible to suppress to the minimum the increase in resistance that occurs when the sheath 21 is inserted through the channel of the endoscope.

Figure 10:
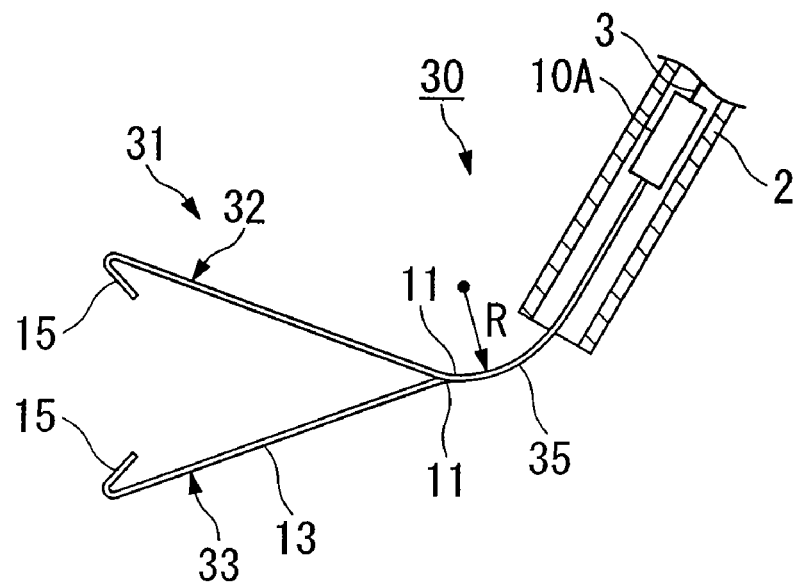
FIG. 10 is a plan view including a partial cross-sectional view showing the essential portion of the high-frequency surgical tool pertaining to a third embodiment of this invention.

Next, a third embodiment is described while referring to FIG. 10.

Components identical to those of the other aforementioned embodiments are given the same reference numerals, and description thereof is omitted.

The point of difference between the first embodiment and the third embodiment is that the parallel portions 35 of the pair of arms 32 and 33 of the elastic grippers 31 of the high-frequency surgical tool 30 of this embodiment are curved in advance.

Specifically, the parallel portions 35 are put into a curved state so that the rectilinear portions 13 of the first embodiment rotate in parallel with the deployment planes S1 and S2 and around an axis that is orthogonal to the direction of forward or backward movement of the pair of arms 32 and 33.

In this embodiment, the radius of curvature R of the parallel portions 35 is, for example, 30 mm.

The radius of curvature R may be in a range from 15 mm to 50 mm.

When the parallel portions 35 are moved into the sheath 2, they undergo elastic deformation, and are stored inside the sheath 2.

When the insertion portion 16A of the endoscope 16 is inserted into a body cavity as shown in FIG. 4, and when the sheath 2 of the high-frequency surgical tool 30 is made to project from the channel in a state in which the distal end of the insertion portion 16A is curved, and when the parallel portions 35 are moved along the direction of curvature of the insertion portion 16A, the direction in which the parallel portions 35 are curved matches the direction of curvature of the insertion portion 16A.

Thus, according to this high-frequency surgical tool 30, it is possible to arrange the pair of arms 32 and 33 in the desired direction, and to enhance operability.

Next, a fourth embodiment is described with reference to FIG. 11.

Components identical to those of the other aforementioned embodiments are given the same reference numerals, and description thereof is omitted.

Figure 11:
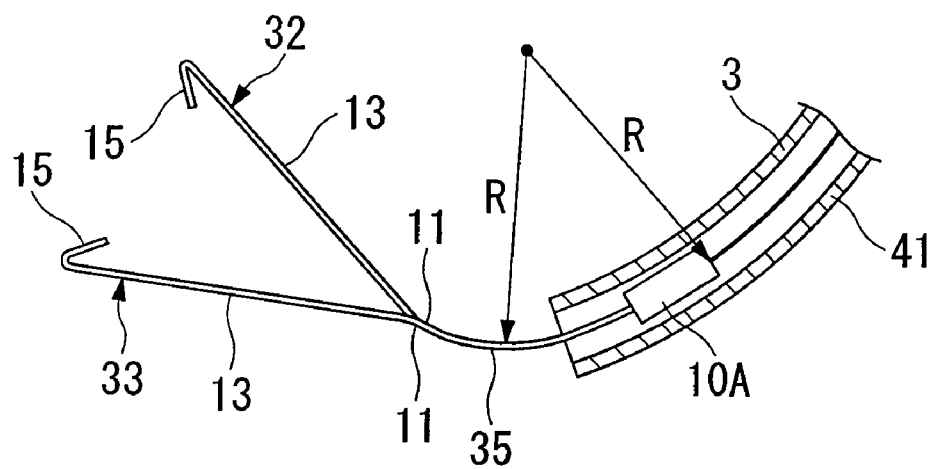
FIG. 11 is a plan view including a partial cross-sectional view showing the essential portion of the high-frequency surgical tool pertaining to a fourth embodiment of this invention.

The point of difference between the third embodiment and the fourth embodiment is that, as shown in FIG. 11, a bent portion is also provided at the distal end of the sheath 41 of the high-frequency surgical tool 40 of this embodiment.

The radius of curvature R of the sheath 41 is a radius of curvature that is approximately identical to the radius of curvature R of the parallel portions 35 of the third embodiment.

According to this high-frequency surgical tool 40, as the sheath 41 is also curved, when the sheath 41 of the high-frequency surgical tool 40 is made to project from the channel in a state in which the distal end of the insertion portion 16A is curved, it is made to project in a state in which it curves along the direction of curvature of the insertion portion 16A, under circumstances where resistance to the channel is lessened.

Since the sheath 41 is flexible, there is concern that the curvature shape may become deformed during transport accompanying shipment and the like.

Figure 12:
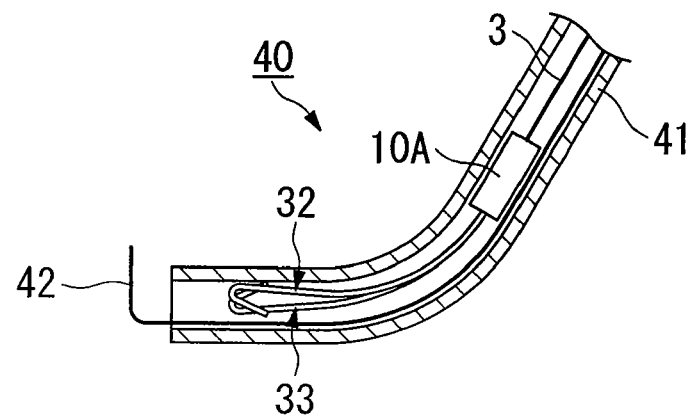
FIG. 12 is a modified example of the fourth embodiment of this invention.

In order to suppress deformation of the sheath, as shown in FIG. 12, a pre-curved shaft-like retainer 42 may be inserted into the sheath 41 from the distal end.

Figure 13:
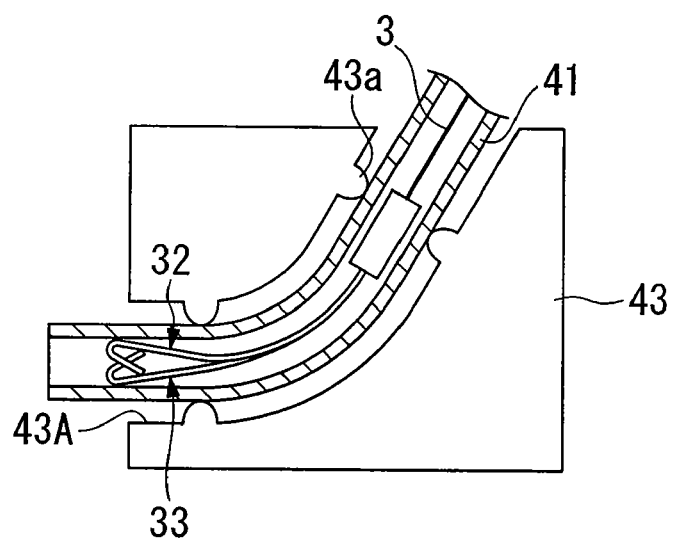
FIG. 13 is a modified example of the fourth embodiment of this invention.

Also, as shown in FIG. 13, a block-shaped retainer 43 may be used to conduct pressure fixing the sheath 41 by inserting the sheath 41 into a block-shaped retainer 43. In this case, the block-shaped retainer 43 is curved in conformity with the radius of curvature of the sheath 41, and in which are disposed a through-hole 43A in which are formed multiple convexities 43a that contact the inner face of the sheath 41.

Figure 14:
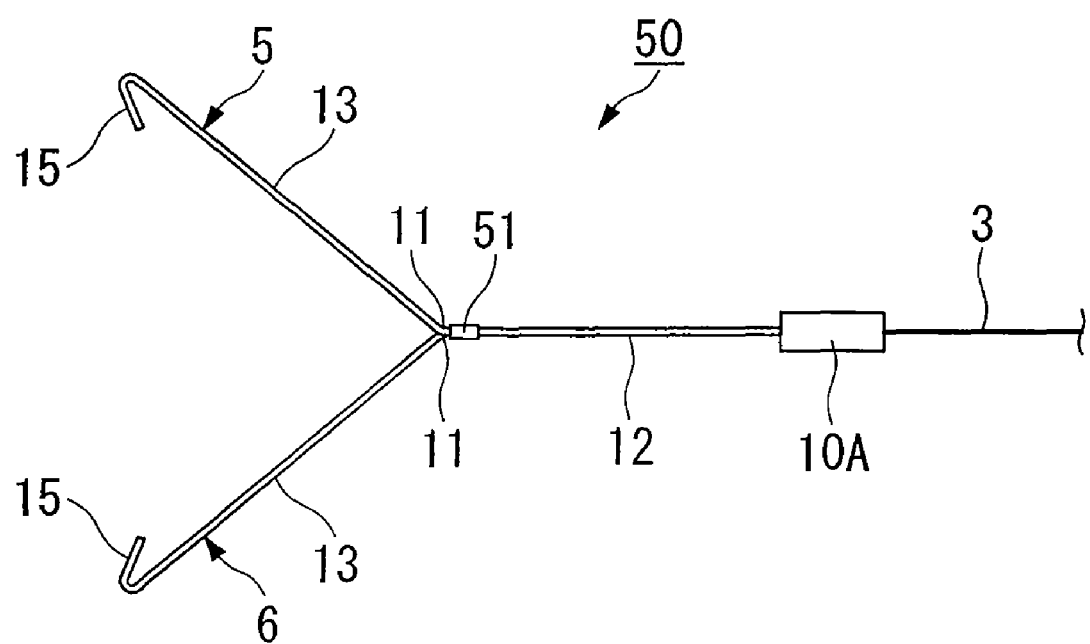
FIG. 14 is a perspective view showing the elastic grippers of the high-frequency surgical tool pertaining to a fifth embodiment of this invention.
Figures 16A, 16B:
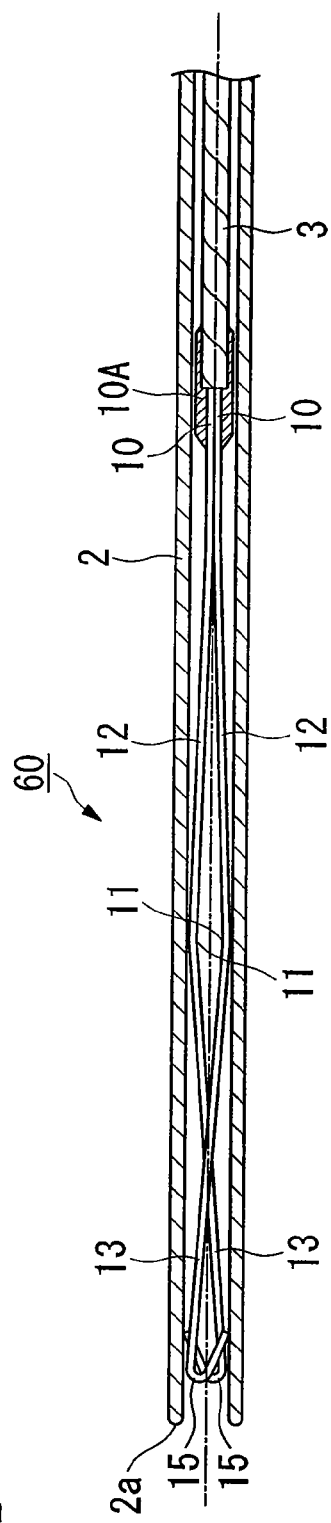
FIG. 16A is a plan view including a partial cross-sectional view showing a state in which the elastic grippers of the high-frequency surgical tool pertaining to the sixth embodiment of this invention are stored inside the sheath.
FIG. 16B is a side view including a partial cross-sectional view showing a state in which the elastic grippers of the high-frequency surgical tool pertaining to the sixth embodiment of this invention are stored inside the sheath.

Next, a fifth embodiment is described while referring to FIG. 14.

Components identical to those of the other aforementioned embodiments are given the same reference numerals, and description thereof is omitted.

The point of difference between the first embodiment and the fifth embodiment is that the high-frequency surgical tool 50 of this embodiment is provided with a fastener 51 which maintains the spacing of the parallel portions 12.

The fastener 51 is arranged in the parallel portions 12 near the bent portions 11.

According to this high-frequency surgical tool 50, even if the pair of arms 5 and 6 are twisted and curved in the sheath 2, it is possible to maintain the mutual spacing of the parallel portions 12 between the connectors 10 and fastener 51, and to enhance the resilience of the parallel portions 12.

Next, a sixth embodiment is described while referring to FIGS. 15A to 16B.

Components identical to those of the other aforementioned embodiments are given the same reference numerals, and description thereof is omitted.

The point of difference between the first embodiment and the sixth embodiment is that the connectors 10 of the pair of arms 61 and 62 of the high-frequency surgical tool 60 of this embodiment are arranged so that the rectilinear portions 13 of the arms 5 and 6 are mutually parallel in parallel planes pertaining to the first deployment plane S1 and second deployment plane S2 which rotate.

That is, the parallel portions 12 are in a mutual torsional relationship from the connectors 10 to the rectilinear portions 13.

By means of this high-frequency surgical tool 60, it is possible to obtain the same actions and effects as the aforementioned first embodiment.

The technical scope of this invention is not limited by the foregoing embodiments, and it is possible to introduce a variety of modifications within a scope that does not deviate from the intent of this invention.

Figure 17:
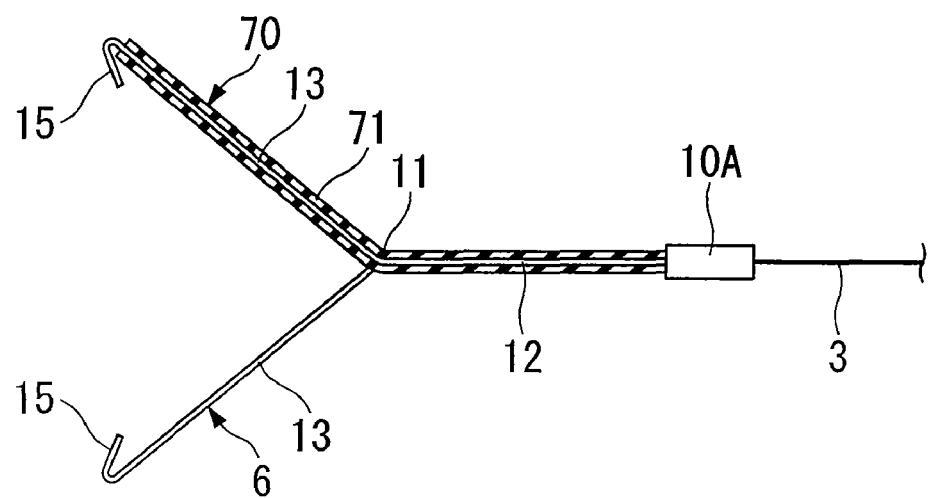
FIG. 17 is a perspective view showing the elastic grippers of the high-frequency surgical tool pertaining to another embodiment of this invention.

For example, in the foregoing embodiments, the elastic linear members of the pair of arms are in a bare state. However, as shown in FIG. 17, it is also acceptable to have an insulating cover 71 on the surface of one of the arms except for the distal clasp 15. In this case, instead of the insulating cover 71, an insulating coating is also acceptable.

Figure 18:
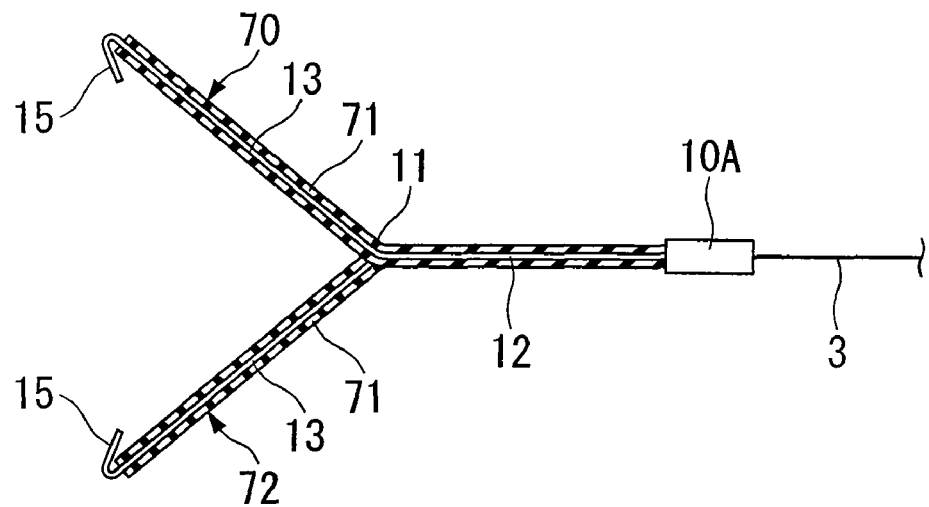
FIG. 18 is a perspective view showing the elastic grippers of the high-frequency surgical tool pertaining to another embodiment of this invention.
Figure 19:
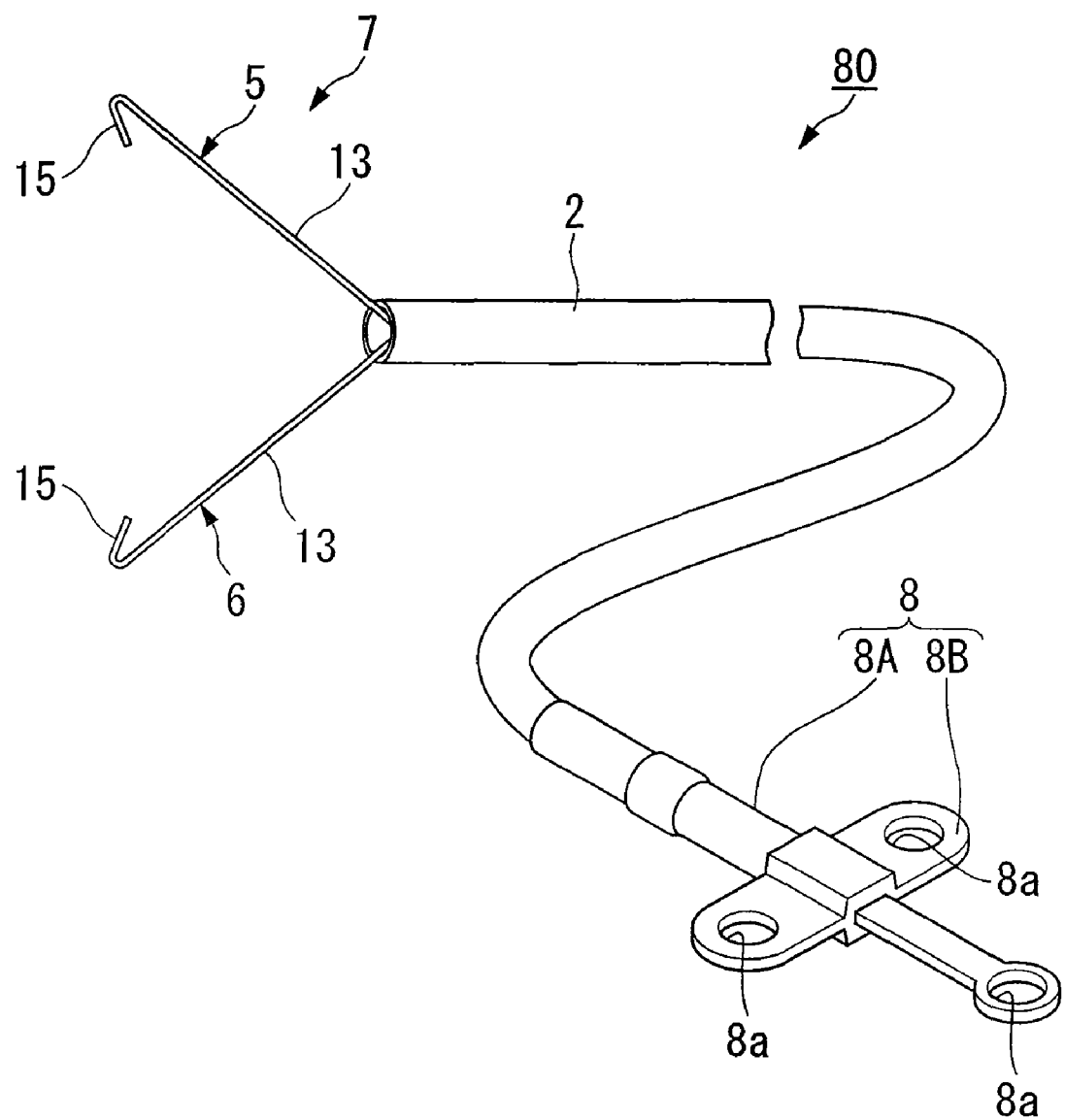
FIG. 19 is a schematic view showing the entirety of a two-armed grasping forceps pertaining to another embodiment of this invention.

Moreover, as shown in FIG. 18, it is also acceptable to have an insulating cover 71 on both arms of the pair of arms 70 and 72.

In this case, it is possible to reduce the area of the conduction parts of the pair of arms 70 and 72 that contact the diseased portion even if the outer circumferential length of the pair of arms 70 and 72 is made longer than that of the first embodiment, and it is possible to increase current density even with the same outer circumferential length.

In the foregoing embodiments, the torsional rigidity of the control wire 3 is reduced, and the rotatability of the elastic grippers relative to the sheath is improved, but it is also acceptable to improve the torque transmission properties of the control wire.

In this case, by rotating the controller of the high-frequency surgical tool, rather than the insertion portion of the endoscope, it is possible to conduct rotation by transmitting rotational torque of the controller to the pair of arms.

In the foregoing embodiments, the treatment tool for an endoscope is a high-frequency surgical tool, but it is not limited thereto, and it is also acceptable to have a two-arm grasping forceps that do not have the functions of high-frequency surgery.

In this case, it is possible to obtain the same actions and effects as the first embodiment by excluding the process of electric conduction but conducting the other processes of the first embodiment.

(Working Example)

Using the high-frequency surgical tool 1 of the first embodiment of this invention, differences in cutting quality due to variations in the outer circumferential length of the distal clasps 15 of the pair of arms 5 and 6 were evaluated by surgery time.

As a method of confirmation, surgery time was measured when gastric mucosa (a fold with a width of approximately 5 mm) was grasped, and cut with conduction of high-frequency current at 60 W of power source output.

The measurement results are shown in Table 1.

TABLE 1

| Outer circumferential length (mm) of distal clasps | Surgery time (seconds) |
| --- | --- |
| 1.26 | (inoperable due to the large amount of time and display of an error message) |
| 1.1 | 5 to 8 |
| 1.0 | 4 to 8 |
| 0.9 | 4 to 5 |
| 0.8 | 3 to 4 |

As outer circumferential length is shortened, surgery time decreases. The desired cutting quality is obtainable with a surgery time equal to or less than 8 seconds.

What is claimed is:

1. A treatment tool for an endoscope which grasps an object of treatment, comprising:
   a flexible sheath;
   a forward-and-backward moving section disposed inside the sheath so as to be capable of freely moving forward and backward, and having a distal end; and
   elastic grippers having a pair of arms whose proximal ends are connected to the distal end of the forward-and-backward moving section, wherein
   each of the pair of arms includes:
   a connector connecting with the forward-and-backward moving section;
   a bent portion disposed closer to a distal end of the arm than the connector, and bent at a fixed angle relative to the forward and backward directions of the forward-and-backward moving section;
   a rectilinear portion maintaining the angle from the bent portion and extending linearly toward the distal end of the arm; and
   a distal clasp disposed at a distal end of the rectilinear portion, for engaging with the object of treatment, wherein
   in conjunction with the forward and backward movement operation of the forward-and-backward moving section, the distal ends of the pair of arms are deployed when the pair of arms are projected from a distal end of the sheath, and the distal ends of the pair of arms are closed by elastic deformation when the pair of arms are moved into the sheath, and wherein
   the rectilinear portions and the bent portions of each of the pair of arms form a first deployment plane and a second deployment plane respectively, the first deployment plane and the second deployment plane being parallel with each other, and
   the first and second deployment planes are distinct.

2. The treatment tool for an endoscope according to claim 1, wherein the pair of arms include parallel portions arranged between the connectors and the bent portions.

3. The treatment tool for an endoscope according to claim 2, wherein the angle of the bent portion is an angle which enables the rectilinear portions to rotate toward a direction parallel to the direction of forward or backward movement of the forward-and-backward moving section when the rectilinear portions contact the distal end of the sheath while the forward-and-backward moving section is moved backward along the sheath.

4. The treatment tool for an endoscope according to claim 3, wherein
   the rectilinear portion of one arm of the pair of arms rotates within the first deployment plane, and the rectilinear portion of the another arm of the pair of arms rotates within the second deployment plane.

5. The treatment tool for an endoscope according to claim 3, wherein
   the parallel portions of the pair of arms are respectively arranged to be mutually parallel in a plane which is orthogonal to a plane in which at least one of the arms rotates.

6. The treatment tool for an endoscope according to claim 3, wherein
   each of the connectors of the pair of arms are arranged to be mutually parallel in a plane which is parallel to a plane in which at least one of the arms rotates.

7. The treatment tool for an endoscope according to claim 2, wherein the parallel portions of the pair of arms are bendable and twistable.

8. The treatment tool for an endoscope according to claim 1, wherein
   the inner diameter of the distal end of the sheath is greater than that of the proximal end of the sheath.

9. The treatment tool for an endoscope according to claim 1, wherein
   the distal clasps are formed by bending at a sharp angle relative to the rectilinear portions toward a center axis of the sheath so as to be disposed closer to the connectors than the distal ends of the rectilinear portions.

10. The treatment tool for an endoscope according to claim 1, wherein
    the forward-and-backward moving section is connected to a treatment energy generator which supplies treatment energy to the pair of arms.

11. The treatment tool for an endoscope according to claim 1, wherein
    the outer circumferential length of the respective distal ends of the pair of arms including at least the distal clasps is equal to or less than 1.1 mm.

12. The treatment tool for an endoscope according to claim 1, wherein when the pair of arms are deployed, the rectilinear portions extend from the bent portion to the distal clasp away from the central axis of the pair of arms.

13. The treatment tool for an endoscope according to claim 1, wherein the pair of arms include bendable and twistable parallel portions arranged between the connectors and the bent portions.

14. The treatment tool for an endoscope according to claim 1, wherein the respective parallel portions of the pair of arms being arranged in a plane that is orthogonal to the first deployment plane and the second deployment plane when the pair of arms are deployed.

15. The treatment tool for an endoscope according to claim 1, wherein when the pair of arms is moved into the sheath, the rectilinear portions press against the distal end of the sheath.

* * * * *

UNITED STATES PATENT AND TRADEMARK OFFICE
CERTIFICATE OF CORRECTION

| | | |
|---|---|---|
| PATENT NO. | : 7,824,407 B2 | Page 1 of 1 |
| APPLICATION NO. | : 11/553084 | |
| DATED | : November 2, 2010 | |
| INVENTOR(S) | : Hironori Yamamoto et al. | |

It is certified that error appears in the above-identified patent and that said Letters Patent is hereby corrected as shown below:

Title Page Item (73) should read

(73) Assignee: Olympus Medical Systems Corp. (JP)

Signed and Sealed this
First Day of March, 2011

David J. Kappos
*Director of the United States Patent and Trademark Office*